(12) United States Patent
Wu et al.

(10) Patent No.: US 7,114,403 B2
(45) Date of Patent: Oct. 3, 2006

(54) FLUID COLLECTION AND APPLICATION DEVICE AND METHODS OF USE OF SAME

(75) Inventors: Yuchang Wu, Hangzhou (CN); Hsiaoho Edward Tung, San Diego, CA (US); Huiyan Guo, San Diego, CA (US); Fei Gao, Hangzhou (CN); Jielin Dai, Hangzhou (CN); Haipeng Hu, Hangzhou (CN)

(73) Assignee: Oakville Hong Kong Co., LTD, (HK)

( * ) Notice: Subject to any disclaimer, the term of this patent is extended or adjusted under 35 U.S.C. 154(b) by 285 days.

(21) Appl. No.: 10/855,155

(22) Filed: May 27, 2004

(65) Prior Publication Data

US 2004/0237674 A1    Dec. 2, 2004

Related U.S. Application Data

(60) Provisional application No. 60/474,788, filed on May 30, 2003.

(51) Int. Cl.
*G01N 1/00* (2006.01)

(52) U.S. Cl. .................................. 73/864.72

(58) Field of Classification Search ............. 73/864.31, 73/864.51, 864.63, 864.71, 864.72, 864.91, 73/864.81; 600/573, 575, 580, 582; 604/1, 604/36, 37, 128, 290, 317, 358
See application file for complete search history.

(56) References Cited

U.S. PATENT DOCUMENTS

| | | | |
|---|---|---|---|
| 2,835,246 A * | 5/1958 | Boettger ..................... 600/570 |
| 3,896,974 A | 7/1975 | McIntosh |
| 4,114,605 A | 9/1978 | McGhee et al. |
| 4,275,149 A | 6/1981 | Litman et al. |
| 4,299,916 A | 11/1981 | Litman et al. |
| 4,596,157 A * | 6/1986 | Laauwe ..................... 73/864.72 |
| 4,635,488 A | 1/1987 | Kremer |
| 4,768,238 A | 9/1988 | Kleinberg et al. |
| 4,771,486 A | 9/1988 | Gutierrez et al. |
| 4,817,632 A | 4/1989 | Schramm |
| 4,853,325 A | 8/1989 | Vodian et al. |
| 4,886,175 A | 12/1989 | Schlaudecker |
| 4,923,798 A | 5/1990 | LeMoine et al. |
| 4,955,745 A | 9/1990 | Vauquelin |
| 5,050,616 A | 9/1991 | Wolff et al. |
| 5,076,474 A | 12/1991 | Hansen |
| 5,211,182 A | 5/1993 | Deutsch et al. |
| 5,246,145 A | 9/1993 | Leoncavallo et al. |
| 5,260,031 A | 11/1993 | Seymour |
| 5,261,572 A | 11/1993 | Strater |

(Continued)

FOREIGN PATENT DOCUMENTS

EP    0 390 984 A1    10/1990

(Continued)

*Primary Examiner*—Robert Raevis (57) ABSTRACT

The present invention is a device for conveniently collecting and storing liquid samples, as well as applying an aliquot of the sample to a test device, such as a lateral flow immunoassay. The present invention comprises an absorbent swab and a dropper container containing an expression means for expressing the collected sample from the swab. After the collected sample has been expressed into the reservoir of the device, the device is capped. The device can be inverted over a test device, the sides of the reservoir squeezed and an aliquot of the sample applied, in a drop-wise manner, to the sample application well of the test device. The present invention is particularly useful for collecting viscous samples, such as saliva or oral fluid, in a drug of abuse testing setting.

47 Claims, 8 Drawing Sheets

U.S. PATENT DOCUMENTS

| | | | |
|---|---|---|---|
| 5,328,058 | A | 7/1994 | Leoncavallo et al. |
| 5,334,502 | A | 8/1994 | Sangha |
| 5,339,829 | A | 8/1994 | Thieme et al. |
| 5,376,337 | A | 12/1994 | Seymour |
| 5,380,492 | A | 1/1995 | Seymour |
| 5,393,496 | A | 2/1995 | Seymour |
| 5,479,937 | A | 1/1996 | Thieme et al. |
| 5,494,646 | A | 2/1996 | Seymour |
| 5,573,009 | A | 11/1996 | Thieme et al. |
| 5,609,160 | A | 3/1997 | Bahl et al. |
| 5,714,341 | A | 2/1998 | Thieme et al. |
| 5,736,322 | A | 4/1998 | Goldstein |
| 5,786,227 | A | 7/1998 | Charlton |
| 5,786,228 | A | 7/1998 | Charlton |
| 5,830,410 | A | 11/1998 | Thieme et al. |
| 5,910,122 | A | 6/1999 | D'Angelo |
| 5,935,864 | A | 8/1999 | Schramm |
| 5,968,746 | A | 10/1999 | Schneider |
| 5,981,293 | A | 11/1999 | Charlton |
| 5,981,300 | A | 11/1999 | Moll et al. |
| 6,022,326 | A | 2/2000 | Tatum et al. |
| 6,102,872 | A | 8/2000 | Doneen et al. |
| 6,150,178 | A | 11/2000 | Cesarczyk |
| 6,223,947 | B1 | 5/2001 | Bernard |
| 6,241,689 | B1 | 6/2001 | Chard et al. |
| 6,248,598 | B1 | 6/2001 | Bogema |
| 6,277,587 | B1 | 8/2001 | Lamster |
| 6,277,646 | B1 | 8/2001 | Guirguis et al. |
| 6,291,178 | B1 | 9/2001 | Schneider |
| 6,303,081 | B1 | 10/2001 | Mink et al. |
| 6,372,513 | B1 | 4/2002 | Nguyen et al. |
| 6,423,550 | B1 | 7/2002 | Jenkins et al. |
| 6,440,087 | B1 | 8/2002 | Sangha |
| 6,443,892 | B1 | 9/2002 | Kidwell |
| 6,464,939 | B1 | 10/2002 | Bachand |
| 6,468,474 | B1 | 10/2002 | Bachand |
| 6,489,172 | B1 * | 12/2002 | Bachand et al. ............ 436/180 |
| 2001/0023324 | A1 | 9/2001 | Pronovost et al. |
| 2002/0004019 | A1 | 1/2002 | Bachand et al. |
| 2002/0015663 | A1 | 2/2002 | Goldstein et al. |
| 2002/0020713 | A1 | 2/2002 | Kis et al. |
| 2002/0146346 | A1 | 10/2002 | Konecke |
| 2002/0150884 | A1 | 10/2002 | Zmuda et al. |
| 2002/0155029 | A1 | 10/2002 | Mink et al. |
| 2002/0192839 | A1 | 12/2002 | Mink et al. |
| 2003/0129673 | A1 | 7/2003 | Schwarz et al. |
| 2003/0138971 | A1 | 7/2003 | D'Aurora |
| 2003/0175992 | A1 | 9/2003 | Toranto et al. |
| 2003/0175993 | A1 | 9/2003 | Toranto et al. |
| 2003/0190259 | A1 | 10/2003 | Alley |

FOREIGN PATENT DOCUMENTS

| | | |
|---|---|---|
| EP | 0 390 984 B1 | 10/1990 |
| EP | 0 392 096 A1 | 10/1990 |
| EP | 0392 096 B1 | 10/1990 |
| EP | 0 455 916 A2 | 11/1991 |
| EP | 0 455 916 A3 | 11/1991 |
| EP | 0 500 172 A1 | 8/1992 |
| EP | 0 542 107 A1 | 5/1993 |
| EP | 0561 322 A1 | 9/1993 |
| EP | 0 455 916 B1 | 2/1996 |
| EP | 0 561 322 B1 | 10/1996 |
| EP | 0 734 684 A1 | 10/1996 |
| EP | 0 734 685 A1 | 10/1996 |
| EP | 0 734 686 A1 | 10/1996 |
| EP | 0 753 148 B1 | 12/1998 |
| EP | 1 216 931 A1 | 6/2002 |
| EP | 1 275 962 A1 | 1/2003 |
| WO | WO 92/16842 | 10/1992 |
| WO | WO 93/11434 | 6/1993 |
| WO | WO 94/07419 | 4/1994 |
| WO | WO 94/18892 | 9/1994 |
| WO | WO 95/02822 | 1/1995 |
| WO | WO 95/07223 | 3/1995 |
| WO | WO 95/27205 | 10/1995 |
| WO | WO 97/20502 | 6/1997 |
| WO | WO 98/44158 | 10/1998 |
| WO | WO 99/06827 | 2/1999 |
| WO | WO 99/22639 | 5/1999 |
| WO | WO 99/22645 | 5/1999 |
| WO | WO 99/27139 | 6/1999 |
| WO | WO 99/50656 | 10/1999 |
| WO | WO 00/15020 | 3/2000 |
| WO | WO 00/20862 | 4/2000 |
| WO | WO 00/25666 | 5/2000 |
| WO | WO 00/64334 | 11/2000 |
| WO | WO 01/08993 A1 | 2/2001 |
| WO | WO 01/49820 A1 | 7/2001 |
| WO | WO 01/81915 A1 | 11/2001 |
| WO | WO 02/07645 A3 | 1/2002 |
| WO | WO 02/04942 A1 | 2/2002 |
| WO | WO 02/16946 A2 | 2/2002 |
| WO | WO 02/016946 A3 | 2/2002 |
| WO | WO 02/059600 A2 | 8/2002 |
| WO | WO 02/059600 A3 | 8/2002 |
| WO | WO 02/082040 A2 | 10/2002 |
| WO | WO 02/082040 A3 | 10/2002 |
| WO | WO 02/096480 A2 | 12/2002 |

* cited by examiner

FLUID COLLECTION AND APPLICATION DEVICE AND METHODS OF USE OF SAME

CROSS-REFERENCE TO A RELATED APPLICATION

This application claims priority of previously filed Unites States Provisional Patent Application Ser. 60/474,788 filed May 30, 2003. The disclosure of the provisional application is incorporated herein by reference.

BACKGROUND OF THE INVENTION

1. Field of the Invention

The present invention relates generally to the fields of fluid collection devices, especially devices for the collection of viscous samples, such as saliva, and methods of use thereof. The collection device of the present invention can be used in conjunction with a test device for detecting an analyte of interest, such as an analyte relating to drug abuse, a disease state, medical condition or etiological agent, in the collected fluid.

2. Description of the Related Art

There are a variety of clinical lateral flow immunoassay devices useful for testing for the presence of an analyte, such as hormones, sugar, adulterants, drugs of abuse and the like, in a sample. In general, these test devices take the form of urine cups with accompanying test cards, dip sticks and cassettes. All of these devices require the use of a potentially infective biological fluid, such as urine, blood or serum that clinical workers find messy and offensive to work with and potentially expose the worker to disease. For example, urine cups are often urinated on the exterior and are easily spilt. Similarly, blood samples require the use of needles for collection, which can expose the clinical worker to a variety of blood-born diseases, such as AIDS and hepatitis.

An additional problem with tests that use urine is that urine can be contaminated with other substances. This is a constant problem in drug of abuse testing setting. Subjects using illegal drugs often attempt to hide the presence of those drugs in their urine, in order to have a negative test. These people do this by adding contaminating substances, such as bleach or ammonia, to the urine sample before giving the sample to the clinical worker. Using saliva as a sample fluid eliminates the contamination problem because the subject is never alone while producing the sample, thus eliminating an opportunity to contaminate the sample.

While the afore mentioned devices have been improving, there continues to be a long felt need for a device that is simple to use, not messy and poses little health risk to the clinical worker. This long felt need is met by the present invention, which is described in detail herein. The present invention contemplates the collection, storage and use of a subject's saliva, which is not classified as a biohazard, by simple, easy, clean and noninvasive methods.

SUMMARY OF THE INVENTION

As a non-limiting introduction to the breath of the present invention, the present invention includes several general and useful aspects, including:

A device for collecting and storing a fluid, and applying an aliquot of the fluid to a test device, comprising: a sample collector having an absorbent member, configured to collect a liquid sample; a receiving member, configured to receive said sample collector; an expression member, configured to express the collected sample from said absorbent member being manually pressed into the expresser member; a reservoir, configured to receive the expressed sample from said sample collector, wherein a portion of said reservoir is flexible, and; an assembly fluidly connected to the reservoir and configured to expel the expressed sample from the device.

A device for collecting and storing a fluid, and applying an aliquot of the fluid to a test device, comprising: a sample collector having a foam or sponge absorbent member, configured to collect a liquid sample; a receiving member, configured to receive said sample collector and having therein an expression member against which said absorbent member is pressed; a reservoir having flexible sides and that receives the expressed sample from said sample collector; and assembly fluidly connected to the reservoir and configured to expel the expressed sample from the device.

A method of collecting a fluid sample, using the device of instant invention, comprising: providing the fluid sample; contacting the fluid sample with said sample collector; inserting said sample collector into said sample collector receiving member; pressing said sample collector against said sample expression member, whereby the fluid sample is expressed from said sample collector; removing said sample collector from said sample collector receiving member; and closing said sample collector receiving member.

A method of applying a collected fluid sample to a test device, using the device present invention, comprising: inverting the device of the present invention; squeezing said sample reservoir; and applying drops of the collected fluid sample to a test device.

A kit, comprising: at least one device of the present invention packaged together with instructions for use of the collection device.

The present invention is a device for collecting and storing liquid samples, as well as applying a portion of a collected sample to a test device. The present invention is particularly useful for viscous biological samples, such as saliva and oral fluid. The present invention comprises an absorbent sample collector, and means of expressing the collected sample from the collector, and reservoir and a dropper assembly.

The present invention recognizes two long felt needs. The first is a need for safer and less offensive means of collecting and using biological fluids, such as urine, blood and serum. The second is a need to stop using such dangerous and offensive biological samples, and to use samples such as oral fluid. Liquid samples, such and saliva and oral fluid have certain characteristics that make them difficult to work with. These characteristics include the high viscosity of saliva and oral fluid, as well as the low concentrations of labile analytes of interest, such as drugs of abuse. Some analytes of interest stick to the sides of containers. In order to test for these analytes, it is necessary to minimize the contact of these analytes and the container holding the sample. The present invention recognizes and addresses these long felt needs.

These embodiments of the present invention, as well as others described herein, can be achieved by using the methods, articles of manufacture and compositions of matter described herein. To gain a full appreciation of the scope of the present invention, it will be further recognized that various embodiments of the present invention can be combined to make additional desirable embodiments of the invention.

BRIEF DESCRIPTION OF THE DRAWINGS

The foregoing summary, as well as the following detailed description may be better understood when read in conjunction with the accompanying drawings, which are incorporated in and form a part of the specification. The drawings serve to explain the principles of the invention and illustrate embodiments of the present invention that are preferred at the time the application was filed. It should be understood, however, that the invention is not limited to the precise arrangements and instrumentalities or the precise arrangement of elements or process steps disclosed.

In the drawings.

DETAILED DESCRIPTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless other wise indicated, shall be understood to have the following meanings:

"Assaying" denotes testing for or detecting the presence of a substance or material, such as, but not limited to, a chemical, an organic compound, an inorganic compound, a metabolic product, a drug or a drug metabolite, an organism or a metabolite of such an organism, a nucleic acid, a protein, or a combination thereof. Optionally, assaying denotes measuring the amount of the substance or material. Assaying further denotes an immunological test, a chemical test, an enzymatic test, and the like.

A "reagent" can be any chemical, including organic compounds and inorganic compounds and combinations thereof. A reagent can be provided in gaseous, solid, or liquid form, or any combination thereof, and can be a component of a solution or suspension. A reagent preferably includes fluids, such as buffers useful in methods of detecting analytes in a sample or specimen, such as anticoagulants, diluents, buffers, assay reagents, specific binding members, detectable labels, enzymes and the like. A reagent can also include an extractant, such as a buffer or chemical, to extract an analyte from a sample or specimen or a sample collection device. For example, a buffer can be used to extract analytes from the sample or specimen, such as LPS from bacteria.

An "analysis device" or "assay device" or "test device" is a device for analyzing a sample or specimen. An analysis device can be used to detect the presence and/or concentration of an analyte in a sample or specimen, or to determine the presence and/or numbers of one or more components of a sample or specimen, or to make a qualitative assessment of a sample or specimen. Analysis devices of the present invention include but are not limited to cuvettes, slides, lateral flow detection devices such as assay strip devices, and columns.

A "lateral flow detection device" or a "lateral flow test device" is a device that determines the presence and/or amount of an analyte in a liquid sample or specimen as the liquid sample or specimen moves through a matrix or material by lateral flow or capillary action, such as an immunochromatographic device. A lateral flow detection device may be used in a vertical or a horizontal orientation or in an orientation between vertical and horizontal. Persons knowledgeable in the art commonly refer to a lateral flow detection device using terms such as "immunochromatographic," "dip sticks," "membrane technology" and "test strips."

"Analyte" is the compound or composition to be measured that is capable of binding specifically to a ligand, receptor, or enzyme, usually and antibody or antigen such as a protein or drug, or a metabolite, the precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments or fragments thereof. An analyte can include and analyte analogue, which is a derivative of an analyte, such as, for example, an analyte altered by chemical or biological methods, such as by the action of reactive chemicals, such as adulterants or enzymatic activity.

"Sample" or "specimen" may be used interchangeably. "Sample" or "specimen" denotes any material to be assayed for the presence and/or concentration of an analyte in a sample or specimen, or to determine the presence and/or numbers of one or more components of a sample or specimen, or to make a qualitative assessment of a sample or specimen. A sample can be the same as a specimen. Preferably, a sample is a fluid sample, preferably a liquid sample. Examples of liquid samples that may be collected using a collection device of the present invention include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

"Subject" refers to any organism, such as an animal or a human. An animal can include any animal, such as a companion animal such as a dog or cat, an agricultural animal such as a pig or a cow, or a pleasure animal such as a horse.

Fluid Collection and Application Device

Figure 1:
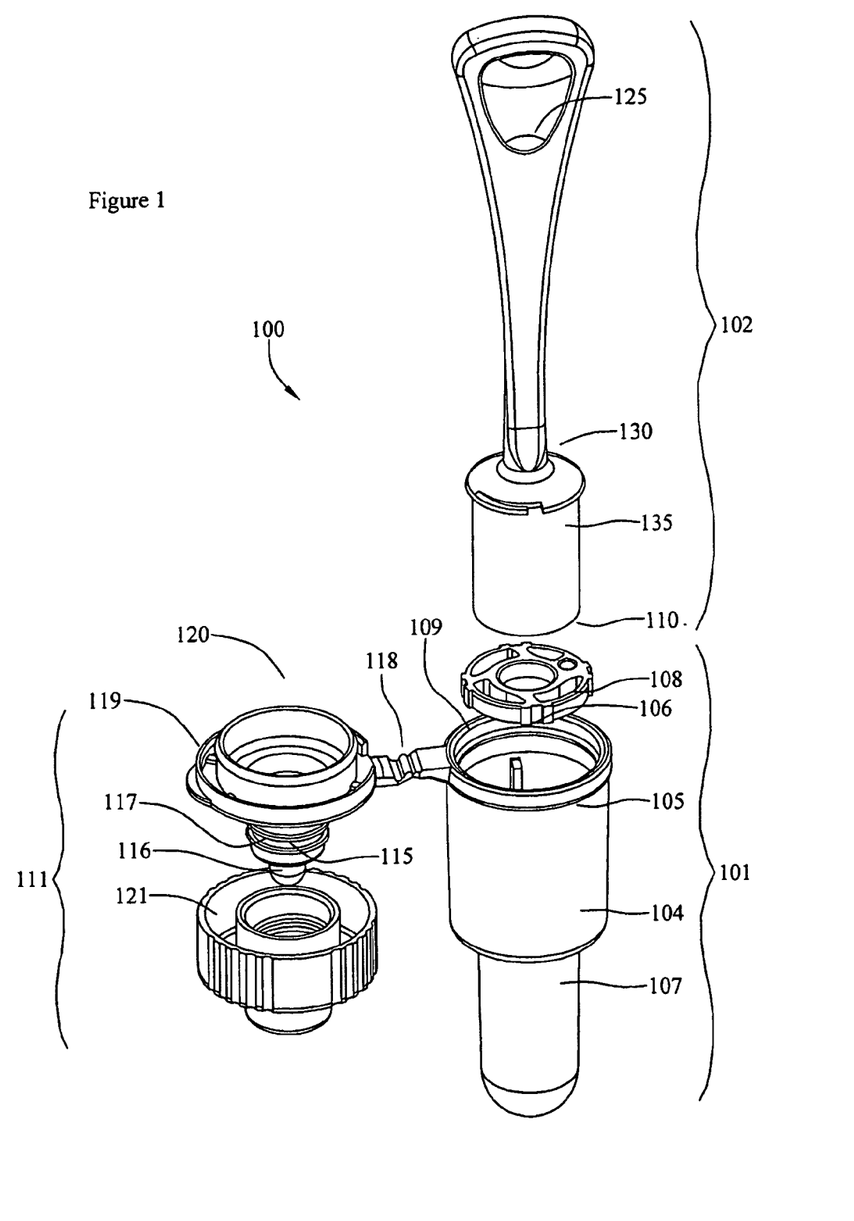
FIG. 1 is a perspective view one embodiment of the present invention 100.
Figure 2:
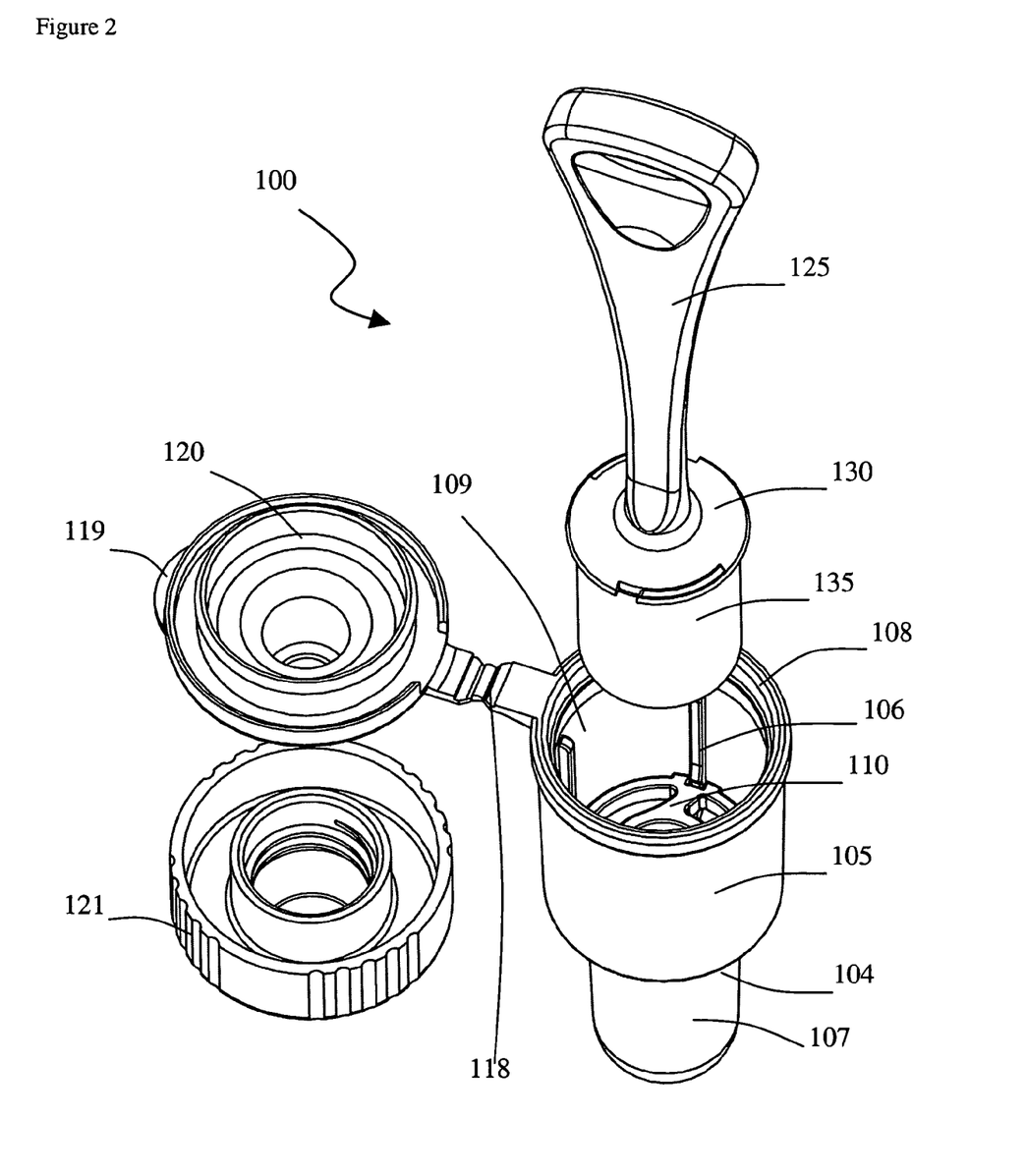
FIG. 2 is another perspective view of the embodiment shown in FIG. 1.
Figure 3:
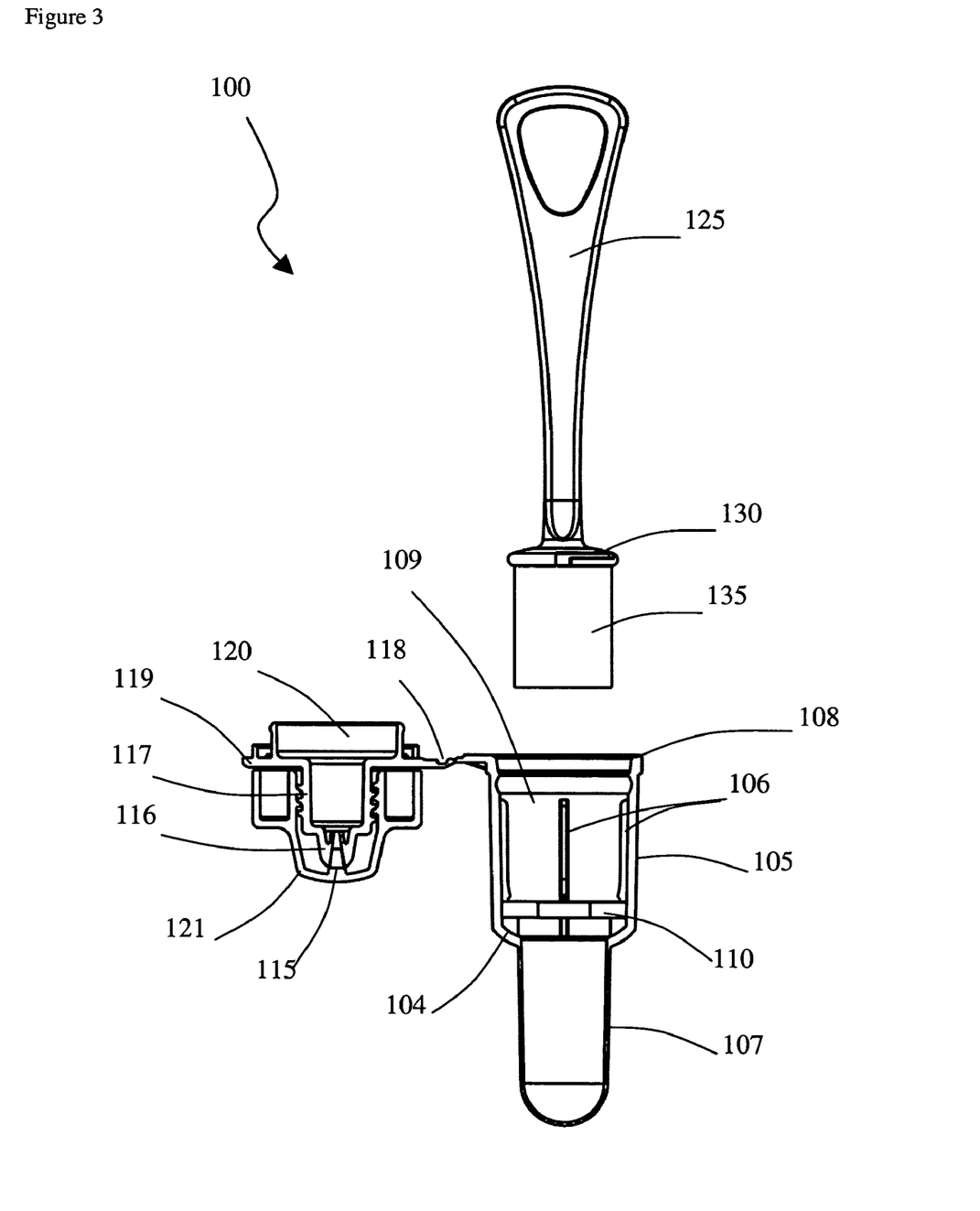
FIG. 3 is a side view of the embodiment shown in FIG. 1. This cartoon illustrates how the absorbent member 135 of the sample collector 102 fits into the tubular barrel 105 of the body 101 of the illustrated embodiment of FIG. 1.

Turning now to the figures, FIGS. 1, 2 and 3 illustrate, by way of example, device 100 for collecting and storing fluids, and applying the fluid to a test device. The device 100 includes a sample collector 102, a receiving member 105, an expression member 110, a reservoir 107, and a dropper assembly 111, which are each described in more detail below.

With reference to FIG. 1, the sample collector 102 includes a handle 125 that can be grasped by an operator. An absorbent member 135 is attached to the handle and is configured to collect a liquid sample. In this regard, the absorbent member 135 can comprise any type of material that can absorb a liquid sample, such as a foam or a sponge. In one embodiment, the handle 125 has an elongate shape and an attachment structure 130, such as a flange, on one end that attaches to the absorbent member 135. It should be appreciated that the size and shape of the handle 125 can vary. Optionally, the absorbent member 135 can be soaked in a solution designed to stimulate salivation by a subject providing a sample of saliva.

The receiving member 105 has walls that define an internal volume sized to receive at least the absorbent member 135 of the sample collector 102. In the illustrated embodiment, the receiving member 105 is barrel-shaped and has a first end that defines an orifice 109 sized to receive the absorbent member 135 therethrough. In one embodiment, the internal walls of the receiving member have one or more longitudinal ribs 106.

The receiving member 105 also has a second end that is attached to the reservoir 107 via an annular shoulder 104. The reservoir 107 is fluidly connected with the internal volume of the receiving member 105. A funnel can connect the receiving member 105 to the reservoir 107. The reservoir 107 has flexible side walls that can be manually pressed inward to force any liquid within the reservoir to be expelled therefrom, such as outward through the dropper assembly 111 when the device 100 is inverted, as described more fully below. The reservoir 107 can have a variety of shapes that are configured to be squeezed to force fluid out of the reservoir 107. For example, the reservoir 107 can have an outwardly-curved shape like a squeeze bulb. The reservoir 107 can also be cylindrical, lobular, spherical, pear, tear, or box shaped.

With reference still to FIG. 1, the expression member 110 is a structure against which the absorbent member 135 can be pressed to deform the absorbent member 135 and expel fluid therefrom. In this regard, as illustrated in FIGS. 2 and 3, the expression member 110 is sized to fit within the receiving member 108 such that the expression member 110 can be interposed within the receiving member 108 between the absorbent member 135 and the reservoir 107, as described more fully below. The expression member 110 has a structure that facilitates deformation of the absorbent member 135 when the absorbent member 135 is pressed against the expression member to express fluid from the absorbent member 135. For example, the expression member 110 can be a ring having radial spokes against which the absorbent member 135 is pressed. The spokes form openings through which sample from the absorbent member 135 can flow into the reservoir 107.

In another example, the expression member can be a wall or disk with one or more holes therethrough. The absorbent member 135 is compressed against the wall and fluid expressed from the absorbent member 135 flows through the one or more holes into the reservoir 107.

As shown in FIG. 1, the dropper assembly 111 is attached to the receiving member 105 through a hinge 118. The hinge attachment keeps the dropper assembly 111 readily attached and available to the receiving member 105, although it should be appreciated that the dropper assembly 111 need not be attached to the receiving member 105. The dropper assembly 111 has a dropper tip 116 with an internal lumen through which fluid can exit the reservoir 107 via a mouth 115 that communicates with the receiving member 105 and reservoir 107. The dropper tip 116 expels liquid in a drop-like fashion pursuant to well-known structures.

The dropper assembly 111 is configured to fit on top of the receiving member 105 such that it mates with the receiving member 105 through the orifice 109. In one embodiment, the dropper assembly 111 mates with the receiving member 105 in a snap-fit fashion such that the dropper assembly 111 snapably attaches to the receiving member 105. In this regard, a tab 119 is located on the dropper assembly 111. The tab 119 can be grasped by a user to unsnap and dislodge the dropper assembly 111 from the receiving member 105 when the dropper assembly 111 is mounted on top of the receiving member 105. When the dropper assembly is mounted on the receiving member 105, it desirably forms a seal with the receiving member 105. A variety of well-known snap-on seals can be used in the structure of the dropper assembly 111. As shown in the embodiment of FIG. 1, a flange 120 protrudes from the bottom surface of the dropper assembly 111. In the embodiment illustrated, flange 120 snuggly mates with a ring 108 at the orifice of the receiving member 105.

It should be appreciated that alternative means can be used to seal the dropper assembly 111 on the mouth 108 of the receiving member 105, and thereby close the device. For example, flange 120 can be constructed with threads configured to mate with a second set of threads on the interior surface of the mouth 108 of the receiving member 105.

The dropper assembly 111 has a cap 121 that is sized to fit over the dropper tip 116. Cap 120 can have a mating engagement with at least a portion of the dropper tip 116, such as in the form of threads that mate with corresponding threads 117 on the dropper tip 116. Additionally, the portion of the cap which covers the mouth 115 of the dropper tip may optionally have a protrusion 410 configured to plug the mouth 115 of the dropper tip 116 (see FIG. 4) and thereby advantageously prevent leaking of the sample.

Figure 4:
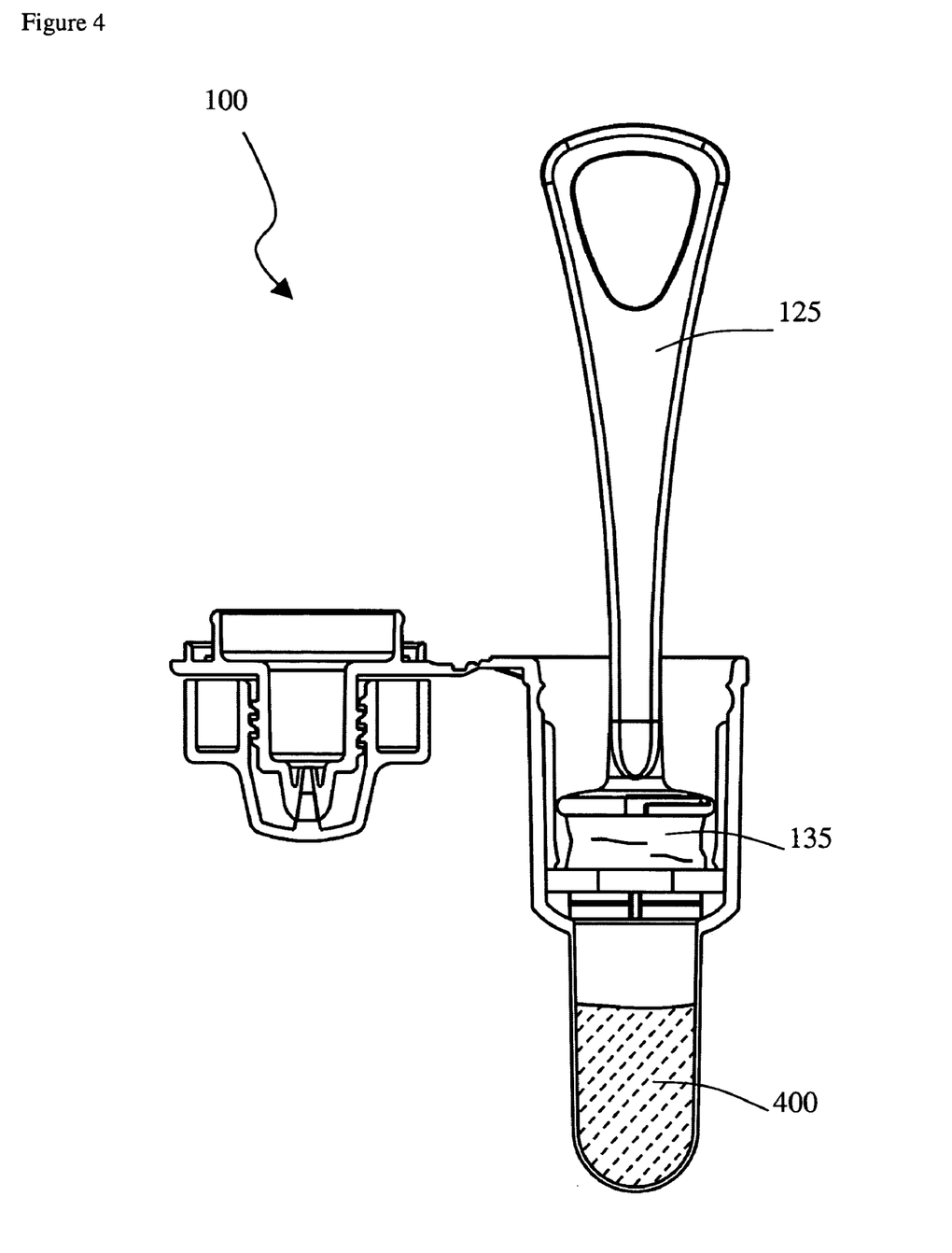
FIG. 4 illustrates expression of a collected sample from the absorbent member 135, into the sample reservoir 107 of the embodiment of FIG. 1.
Figure 5:
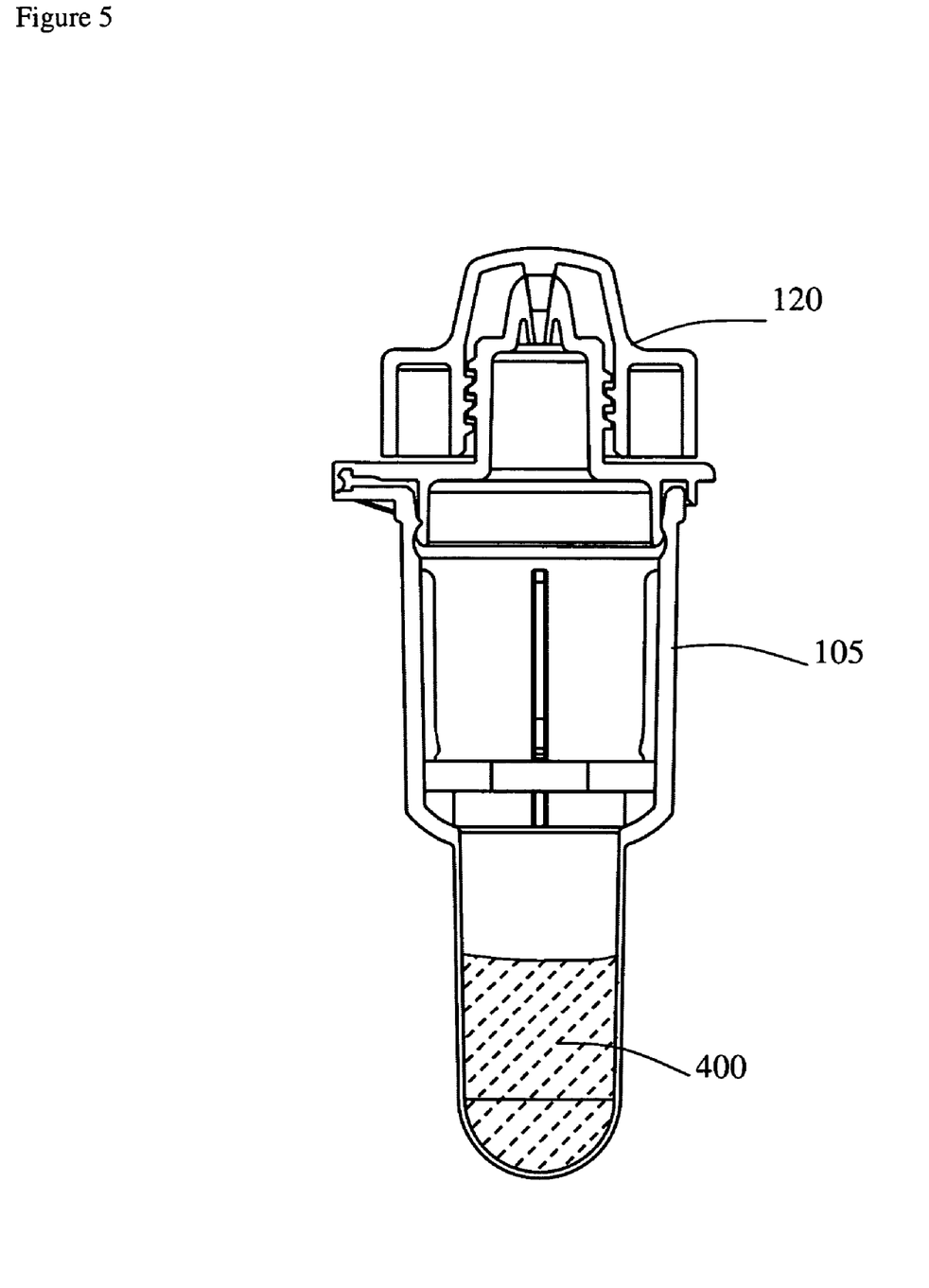
FIG. 5 is a side view of the embodiment shown in FIG. 1, illustrating the closed position of the snap lid 111, after a sample has been expressed into the sample reservoir 107.

FIG. 3 illustrates the initial use of the device. Here, the absorbent member 135 of the sample collector 102 is positioned above and inserted into the receiving member 105. As illustrated in FIG. 4, the absorbent member 135 of the sample collector 102 is pressed against the expression member 110, to express at least a portion of the collected sample 400 into the reservoir 107. After expression of the sample 400 into the receiving member 107, the sample collector 102 may be discarded and the receiving member 105 closed by bending hinge 118 until the dropper assembly 111 is mounted on the receiving member 105. In the case of the present example, the dropper assembly 111 is pressed onto the receiving member 105 until it snaps in place and makes a tight seal. It must be recognized that alternative sealing methods could be used to close the device. For example, the dropper assembly 111 and receiving member 105 can be configured to mate in a screw-cap fashion using mating threads.

Figure 6:
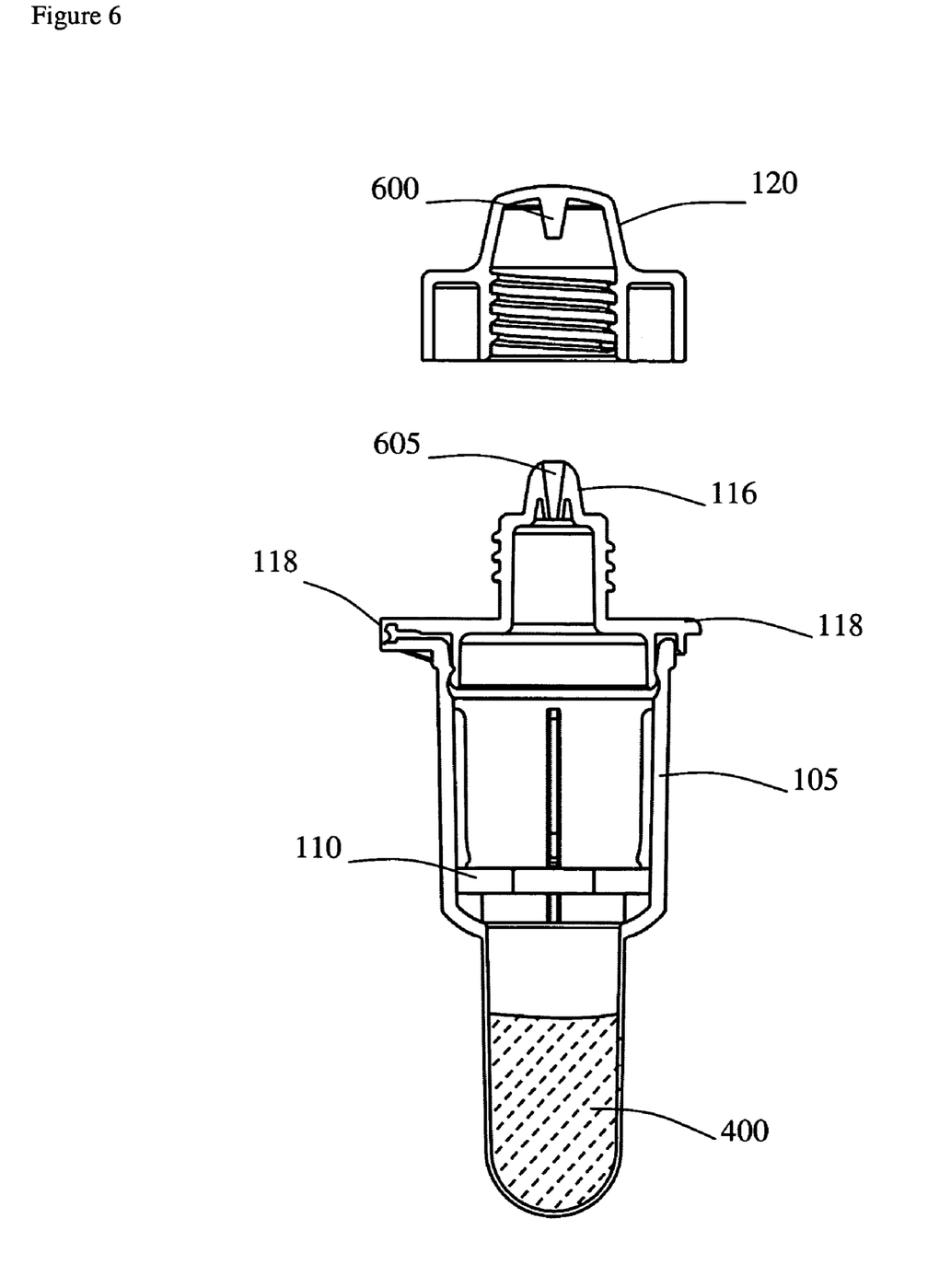
FIG. 6 is a side view of the embodiment shown in FIG. 1, after the screw cap 120 has been removed from the exterior side of the snap lid 111.
Figure 7:
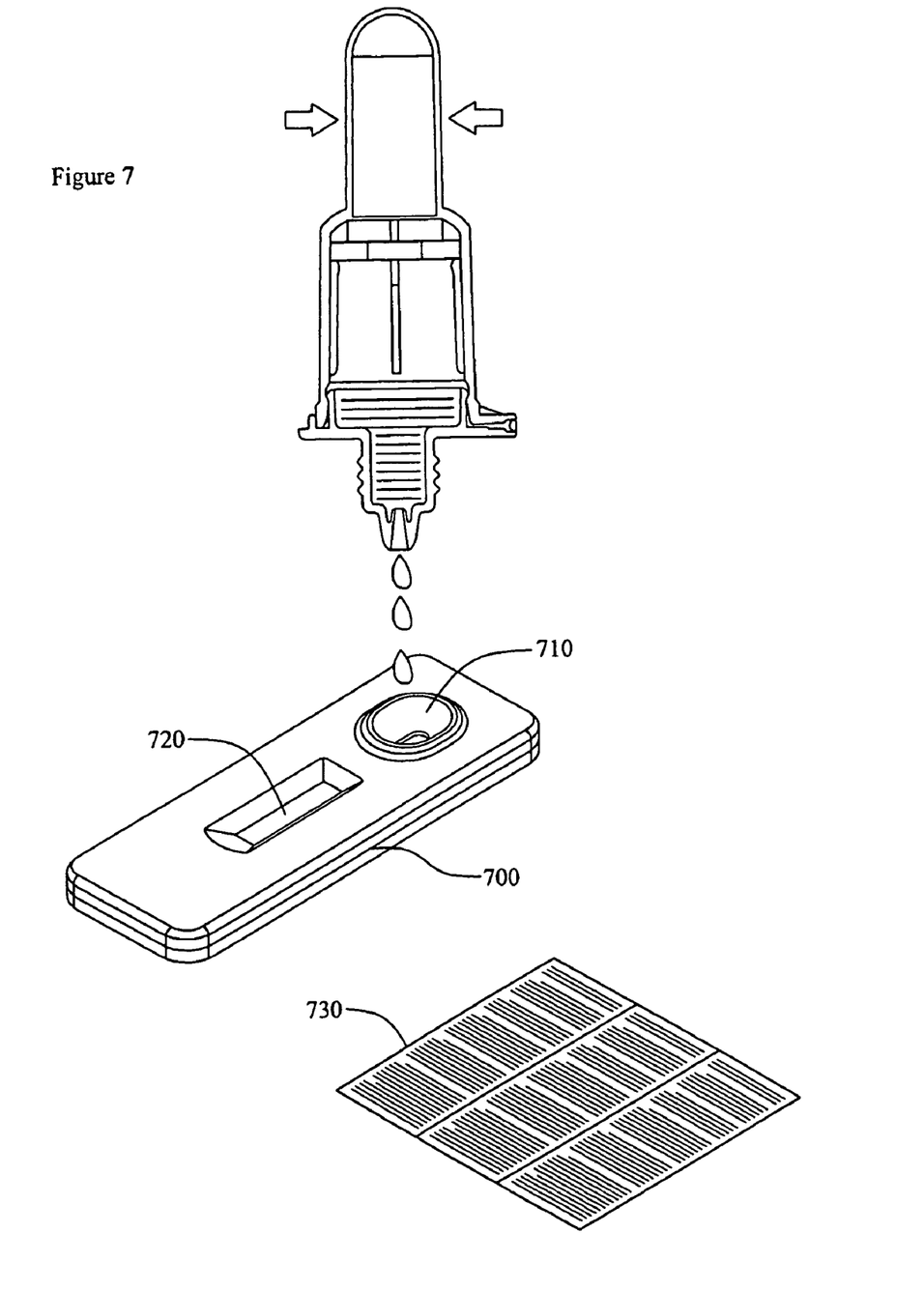
FIG. 7 is a side view of the embodiment of FIG. 1, in the inverted position and applying an aliquot of the collected sample, in a drop-wise manner, to the sample application well 710 of a test device 700.

As illustrated in FIG. 6, cap 120 can be removed from the dropper assembly 111. In the case of the example presented, the cap 120 is unscrewed from the dropper assembly 111. After the cap 120 is removed, the device can be inverted and drops of sample conveniently expelled, for example, by manual pressure on the sides of the reservoir 107. It is also contemplated that the device can be opened by removing the dropper assembly 111 from the receiving member 105, and an aliquot of sample removed with a pipette.

Liquid Samples

The sample collected by the sample collector 102 is any material to be assayed for the presence and/or concentration of an analyte in a sample or specimen that can be absorbed by the absorbent member 135. Preferably, the sample is a fluid sample, preferably a liquid sample. Examples of liquid samples that may be collected using a device of the present invention include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semi-solid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

The present invention is particularly useful for the collection of viscous samples, such as oral fluids and saliva. The absorbent member 135 can be configured to fit comfortably in to the mouth of a subject, such as a human. The absorbent member 135 may additionally be constructed of a sponge or foam designed to be chewed. In one aspect of the present invention, the absorbent member 135 is soaked in a solution to stimulate salivation. When the absorbent member 135 is placed in a subject's mouth, the subject can suck and chew the absorbent member 135 until the absorbent member 135 is filled with sample.

In another setting, the present invention may be used to conveniently collect urine from a subject without the use of a cup. For example, the absorbent member 135 may be held in the urine stream of a pet, such as a dog or cat, or a young child.

Methods of Use

Figure 8:
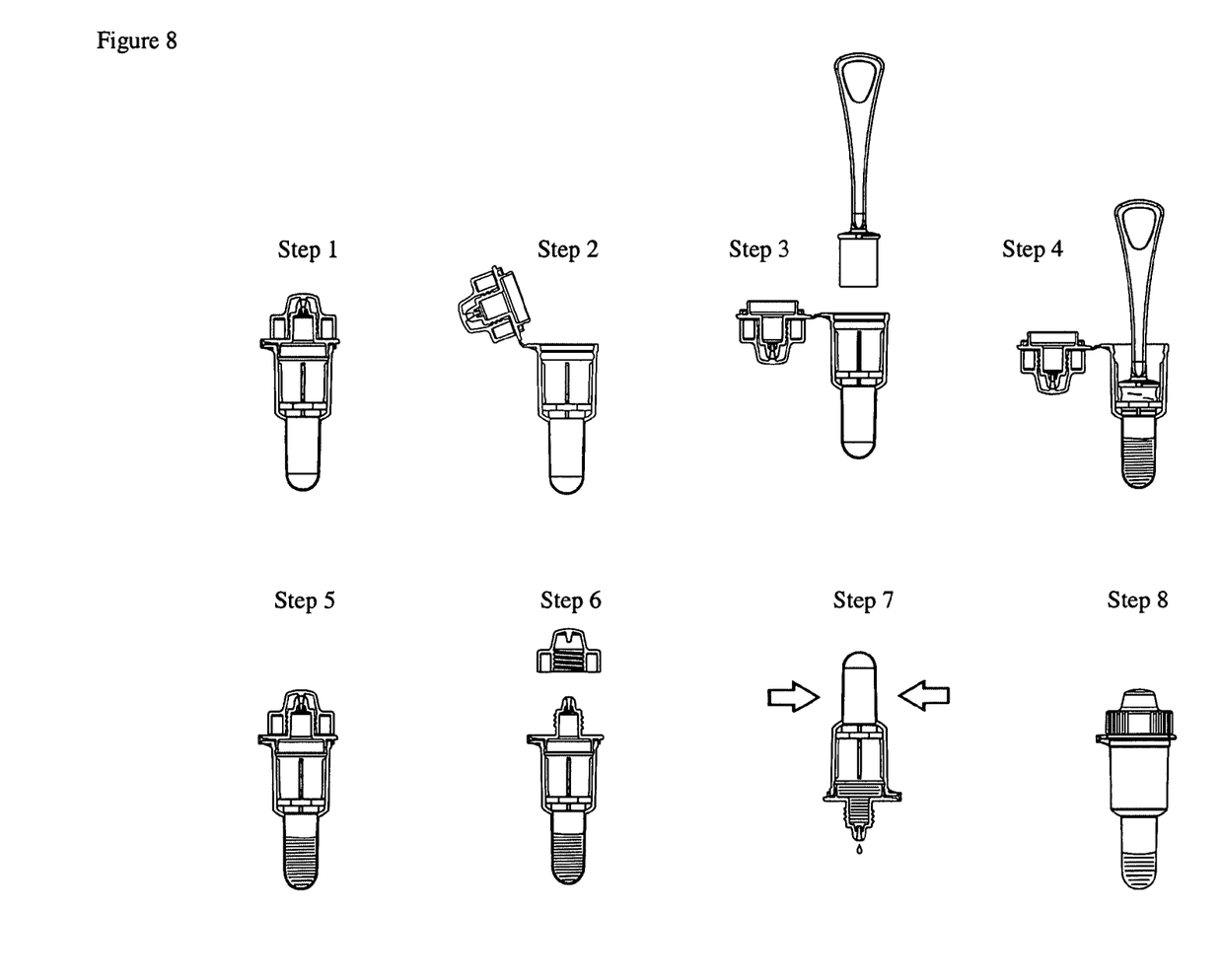
FIG. 8 is a cartoon illustrating the steps of sample collection, use and storage, using the embodiment of the present invention illustrated in FIGS. 1–7.

FIG. 8 illustrates, by way of example, one method of use of the present invention. First, a fluid sample must be collected. In many cases, a sample of saliva may be collected by placing the absorbent member 135 of the sample collector 102 into the fluid to be collected, for example the mouth of a subject. The subject would hold the absorbent member 135 in his mouth until it is filled with saliva. In some aspects of the present invention, the absorbent member 135 is hard to the touch prior to use, due to soaking in salivation promotion solutions and drying. As the absorbent member 135 absorbs saliva, it becomes progressively softer. When the absorbent member 135 is completely soft, it is filled with sample. Depending upon the rate of subject salivation and the amount the subject chews the absorbent member 135, it may take 5 to 10 minutes to collect the sample, but it may take more or less time to collect the sample.

In general, the body 101 of the device can be provided closed (see FIG. 8, Step 1). As shown in Steps 2 and 3, the body 101 is opened, by displacing the dropper assembly 111 from the orifice of the receiving member 105. The absorbent member 135, now soaked with sample, is inserted into the interior of the receiving member 105. Next, the absorbent member 135 is pressed against the expression member 110, causing sample to be expressed from the absorbent member 135. The expressed sample passes through perforations or holes in the expression member 110 and into the receiving member 107. The used sample collector 102 is conveniently discarded, for example, in the trash.

At this point, the body 101 of the device is closed, as illustrated in FIG. 8, Step 5. The sample may be stored in this state, for use at a later time, or a portion of the sample may be tested. If the sample is to be stored, it may be stored by any convenient means appropriate for the particular kind of sample collected. In many cases, the sample is stored in the refrigerator or possibly the freezer. It is important to select a storage means that preserves the sample with as little degradation as possible.

When an aliquot of the sample is to be used, the cap 120 is removed from the dropper assembly 111. The device is inverted, causing the collected sample to flow from the reservoir 107 to the dropper tip 116. Pressure is applied to the reservoir 107 sides, illustrated by the arrows of FIG. 8, Step 7. The applied pressure causes the expulsion of an aliquot of sample in a drop-wise manner. Following use, the device is returned to the upright position and re-capped. The remaining sample may be stored for later use, or thrown away.

Kits

The present invention may be provided as a kit, including at least one device of the present invention, packaged together with instructions for use. As an added convenience, the device can be packaged with one or more test devices and instructions for their use.

EXAMPLES

Drug Testing for Employment:

An employee is sent to an independent drug-testing center. At the center, the employee is given the sample collector 102 of the present invention and instructed to suck on it for a short period of time, such as 10 to 15 minutes. After the absorbent member 135 has become soft and pliable, the technician retrieves the sample collector 102 from the employee and the employee is allowed to leave.

The technician opens the body of the device of the present invention that was packaged with the sample collector. Then the technician inserts the absorbent member 135 into the receiving member 105 and presses the absorbent member 135 against the expression member 110 within the receiving member 105. When sufficient sample has been expressed from the absorbent member 135, the technician throws the sample collector away and caps the body 101 of the device.

The technician then places a test device on the counter. Any test device configured to analyze saliva can be used in conjunction with the device of the present invention when the collected sample is saliva. For example, a multi-drug rapid immunoassay test panel cassette can be used. Similar devices that take a urine or blood sample are commonly used in such settings. However, these devices can be advantageously configured to function with a saliva sample. Single drug tests are available. More conveniently, multi-drug rapid immunoassay test panel cassettes test the sample for the presence of one or more drugs, such as cocaine, methamphetamines, barbiturates, opiates, marijuana, acetaminophen and tricyclic antidepressants. Employers want to determine if an employee or potential employee is using illegal drugs. Emergency rooms want to determine what drug an over-dose patient has used.

Next, the technician uncaps the device, inverts the device over the sample application well of the test device, and by squeezing the sides of the reservoir 107, according to the test device instructions, applies an aliquot of the saliva sample. For example, 3 to 5 drops of the saliva sample may be applied to the sample well of the test device cassette. The technician then returns the device to the upright position and seals the dropper assembly 111 with the cap 121.

After applying the saliva aliquot to the test device, the test generally runs automatically. The technician receives the test results within a few minutes of sample application to the test device. The remaining sample is stored or shipped to another laboratory for confirmation testing of the test results.

Pet Dog Urine Analysis for Bladder Infection:

A pet owner takes her dog to the vet because the housetrained dog is urinating an excessive number of times and in the house. The veterinarian suspects that the dog may have a bladder infection. To determine if this is true, the vet takes the dog outside. When the dog urinates, the vet holds the absorbent member 135 of the present invention in the urine stream. The vet then expresses the collected urine into the reservoir of the present invention. To test for a blabber infection, the vet expels a few drops of the urine onto pH paper, which indicates that the dog's urine is in the alkaline range found in dogs with bladder infections. To confirm his findings, the vet expresses a drop of urine onto a slide and examines the urine under a microscope. The vet observes white blood cells in the urine, confirming that the dog has a bladder infection. The vet prescribes a course of antibiotics for the dog, which subsequently recovers from the bladder infection.

We claim:
1. A device for collecting and storing a fluid, and applying an aliquot of the fluid to a test device, comprising:
   a. a sample collector having an absorbent member, configured to collect a liquid sample;
   b. a receiving member, configured to receive said sample collector;
   c. an expression member, configured to express the collected sample from said absorbent member being manually pressed into the expression member;
   d. a reservoir, configured to receive the expressed sample from said sample collector, wherein a portion of said reservoir is flexible, and;
   e. an assembly fluidly connected to the reservoir and configured to expel the expressed sample from the device.

2. The device of claim 1, wherein said sample collector further comprises a handle and a handle attachment means, wherein said absorbent member is attached to said handle attachment means.

3. The device of claim 2, wherein said absorbent member further comprises a foam.

4. The device of claim 2, wherein said absorbent member further comprises a sponge.

5. The device of claim 2, wherein said absorbent member is treated with a solution that stimulates salivation in a subject from which the sample is to be collected.

6. The device of claim 2, wherein said handle is substantially rigid and optionally comprises a textured grip for holding said sample applicator.

7. The device of claim 1, said receiving member further comprising a barrel having first and second ends and an exterior and an interior, said first end further comprising an orifice providing access to said interior of said barrel for receiving said sample collector and said second end being attached to said reservoir.

8. The device of claim 7, the interior surface of said barrel interior having one or more longitudinal ribs.

9. The device of claim 7, said barrel second end further comprising an annular shoulder connecting to said reservoir.

10. The device of claim 7, said barrel second end further comprising a funnel connecting to said reservoir.

11. The device of claim 7, said first end of said barrel having first threads.

12. The device of claim 11, said assembly having second threads shaped to thread with said first threads of said barrel.

13. The device of claim 1, said expression means further comprising a ring having radial spokes against which said absorbent member is manually pressed and through which said sample flows into said reservoir.

14. The device of claim 1, said expression means further comprising a wall against which said absorbent member is manually pressed and said wall having an aperture in fluid communication with said reservoir and through which the sample flows to said reservoir.

15. The device of claim 1, said expression means further comprising a disk against which said absorbent member is manually pressed and said wall having one or more apertures in fluid communication with said reservoir and through which said sample flows to said reservoir.

16. The device of claim 1, said reservoir having flexible sides such that the sides of said reservoir can be manually pressed inward, whereby, when said device is in the inverted position, manually applied pressure on the reservoir causes expression of the sample from said assembly, in a drop-wise fashion.

17. The device of claim 1, wherein said reservoir is shaped like a squeeze bulb.

18. The device of claim 1, wherein said reservoir is cylindrically, lobularly, spherically, pear, tear-drop or box-like shaped.

19. The device of claim 1, wherein said assembly is configured to expel liquid as a stream, drops, droplets, or a mist.

20. The device of claim 7, said assembly being removably attached to the exterior surface of said first end of said barrel by a hinge member.

21. The device of claim 1, said assembly further comprising: a lid having a dropper tip, said dropper tip having a mouth.

22. The device of claim 21, wherein said lid is adapted to tightly seal a first end of said receiving member.

23. The device of claim 1, said assembly further comprising a bottom that is snapably attachable to said receiving member and thereby closes said receiving member.

24. The device of claim 1, wherein said reservoir is adapted to allow for squeezing and when the device of claim 1 is in an inverted position said squeezing of said reservoir causes drops of the sample to be expelled from the device of claim 1 through said orifice of said dropper tip.

25. A device for collecting and storing a fluid, and applying an aliquot of the fluid to a test device, comprising:
  a sample collector having a foam or sponge absorbent member, configured to collect a liquid sample;
  a receiving member, configured to receive said sample collector and having therein an expression member against which said absorbent member is pressed;
  a reservoir having flexible sides and that receives the expressed sample from said sample collector; and
  an assembly fluidly connected to the reservoir and configured to expel the expressed sample from the device.

26. The device of claim 25, wherein said absorbent member is treated with a solution that stimulates salivation in a subject from which the sample is to be collected.

27. The device of claim 25, wherein said handle is substantially rigid and optionally comprises a textured grip for holding said sample applicator.

28. The device of claim 25, said receiving member further comprising a barrel having first and second ends and an exterior and an interior, said first end further comprising an orifice providing access to said interior of said barrel for receiving said sample collector and said second end being attached to said reservoir.

29. The device of claim 28, said first end of said barrel having first threads.

30. The device of claim 29, said assembly having second threads shaped to thread with said first threads of said barrel.

31. The device of claim 28, the interior surface of said barrel interior having one or more longitudinal ribs.

32. The device of claim 28, said barrel second end further comprising an annular shoulder connecting to said reservoir.

33. The device of claim 28, said barrel second end further comprising a funnel connecting to said reservoir.

34. The device of claim 25, said expression means further comprising a ring having radial spokes against which said absorbent member is manually pressed and through which said sample flows into said reservoir.

35. The device of claim 25, said expression means further comprising a wall against which said absorbent member is manually pressed and said wall having an aperture in fluid communication with said reservoir and through which the sample flows to said reservoir.

36. The device of claim 25, said expression means further comprising a disk against which said absorbent member is manually pressed and said wall having one or more apertures in fluid communication with said reservoir and through which said sample flows to said reservoir.

37. The device of claim 25, said reservoir having flexible sides such that the sides of said reservoir can be manually pressed inward, whereby, when said device is in the inverted position, manually applied pressure on the reservoir causes expression of the sample from said assembly, in a drop-wise fashion.

38. The device of claim 25, wherein said reservoir is shaped like a squeeze bulb.

39. The device of claim 25, wherein said reservoir is cylindrically, lobularly, spherically, pear, tear-drop or box-like shaped.

40. The device of claim 25, wherein said assembly is configured to expel liquid as a stream, drops, droplets, or a mist.

41. The device of claim 28, said assembly being removably attached to the exterior surface of said first end of said barrel by a hinge member.

42. The device of claim 25, said assembly further comprising: a lid having a dropper tip, said dropper tip having a mouth.

43. The device of claim 42, wherein said lid is adapted to tightly seal a first end of said receiving member.

44. The device of claim 25, the assembly further comprising a bottom that is snapably attachable to said receiving member and thereby closes said receiving member.

45. A method of collecting a fluid sample, using the device of claim 1 or 25, comprising:
  a. providing the fluid sample;
  b. contacting the fluid sample with said sample collector;
  c. inserting said sample collector into said sample collector receiving member;
  d. pressing said sample collector against said sample expression member, whereby the fluid sample is expressed from said sample collector;
  e. removing said sample collector from said sample collector receiving member; and
  f. closing said sample collector receiving member.

46. A method of applying a collected fluid sample to a test device, using the device of claim 1 or 25, comprising:
  a. inverting the device of claim 1;
  b. squeezing said sample reservoir; and
  c. applying drops of the collected fluid sample to a test device.

47. A kit, comprising: at least one device of claim 1 or 25 packaged together with instructions for use of said test device.

* * * * *